US010324040B2

(12) United States Patent
 Aguilera Andoaga et al.

(10) Patent No.: US 10,324,040 B2
(45) Date of Patent: Jun. 18, 2019

(54) QUANTITATIVE ANALYSIS METHOD FOR ANALYZING THE ELEMENTAL COMPOSITION OF MATERIALS BY MEANS OF LIBS TECHNIQUE

(71) Applicant: UNIVERSIDAD PUBLICA DE NAVARRA, Pamplona (Navarra) (ES)

(72) Inventors: Jose Antonio Aguilera Andoaga, Pamplona (ES); Carlos Aragon Garbizu, Pamplona (ES)

(73) Assignee: UNIVERSIDAD PUBLICA DE NACARRA, Pamplona (ES)

( * ) Notice: Subject to any disclaimer, the term of this patent is extended or adjusted under 35 U.S.C. 154(b) by 342 days.

(21) Appl. No.: 15/110,476

(22) PCT Filed: Jan. 8, 2014

(86) PCT No.: PCT/EP2014/050224
§ 371 (c)(1),
(2) Date: Jul. 8, 2016

(87) PCT Pub. No.: WO2015/104049
PCT Pub. Date: Jul. 16, 2015

(65) Prior Publication Data
US 2016/0334336 A1 Nov. 17, 2016

(51) Int. Cl.
*G01N 21/71* (2006.01)
*G01J 3/443* (2006.01)

(52) U.S. Cl.
CPC .......... *G01N 21/718* (2013.01); *G01J 3/443* (2013.01)

(58) Field of Classification Search
CPC ........ G01J 3/443; G01N 21/71; G01N 21/718
See application file for complete search history.

(56) References Cited

U.S. PATENT DOCUMENTS

2012/0029836 A1  2/2012 Hermann

OTHER PUBLICATIONS

Aguilera, J.A., Aragon, C., Cristoforetti, G., Tognoni, E., "Application of Calibration-Free Laser-Induced Breakdown Spectroscopy to Radially Resolved Spectra from a Copper-Based Alloy Laser-Induced Plasma," Spectrochimica Acta Part B, 64, 2009, pp. 685-689, www.elsevier.com/locate/sab.

(Continued)

*Primary Examiner* — Kyle R Quigley
(74) *Attorney, Agent, or Firm* — Kunzler Bean & Adamson

(57) ABSTRACT

The quantitative analysis method for analyzing the composition of materials of the invention is based on a functional relationship (curve $C\sigma$) between line intensity and the concentration of the element in the material. The method comprises: obtaining characteristic parameters, selecting the spectral lines of neutral atoms and ions of the elements of interest, obtaining their atomic data; calculating, for the selected lines, a line crosssection; measuring line intensities; determining the concentrations of the elements of interest by means of fitting two graphs $C\sigma$, one for neutral atoms and another for ions with a unit charge, the fitting being performed by means of an iterative algorithm which compares the experimental graphs with the curves $C\sigma$ calculated with a plasma model; calculating, for the data of the graphs $C\sigma$, the product of line optical depth by Lorentzian width; evaluating, for the data of the graphs $C\sigma$, a condition on the validity limit of the model, the datum for which the mentioned product is greater being eliminated if the condition is not complied with; repeating the three preceding steps until all data comply with the mentioned condition. The invention has the advantage of not requiring prior calibrations.

8 Claims, 6 Drawing Sheets

(56) References Cited

OTHER PUBLICATIONS

Aragon, C., Penalba, F., Aguilera, J.A., "Curves of Growth of Neutral Atom and Ion Lines Emitted by a Laser Induced Plasma," Spectrochimica Acta Part B, 60, 2005, pp. 879-887, www.elsevier.com/locate/sab.

QUANTITATIVE ANALYSIS METHOD FOR ANALYZING THE ELEMENTAL COMPOSITION OF MATERIALS BY MEANS OF LIBS TECHNIQUE

FIELD OF THE INVENTION

The present invention relates to the analysis of the composition of materials by means of the so-called laser-induced breakdown spectroscopy (LIBS) or laser-induced plasma spectroscopy technique.

BACKGROUND

The LIBS technique is based on generating a plasma by focusing a pulsed laser beam on a material. The radiation emitted by the plasma is detected by the LIBS system, a spectrum containing a continuum emission as well as the spectral lines of the elements forming the material being obtained. It is possible to determine the concentrations of said elements in the material by analyzing the spectrum.

Due to the optical nature of the energy source with which the plasma is generated, the LIBS technique is applied at a distance, without contacting the material being analyzed. Furthermore, a prior material preparation is not necessary. The technique is applicable to a solid or liquid sample surrounded by a specific ambient gas or in vacuum, or by focusing the laser directly on a liquid or a gas which is contained in a recipient or which is flowing. These characteristics make the LIBS technique a versatile analysis method with applications such as steel analysis in melting furnaces, analysis in plastic recycling, control of laser cleaning process for cleaning the contaminated stone of a building, detection of metal contaminants in the environment, detection of explosives, chemical analysis in space missions, etc.

A method for determining the concentration of atomic species in gases and solids by means of LIBS technique has been described in application WO 97/15811. In this method, at least two emission intensities of an atomic species in the sample are measured during a time interval with selected delay and length of time, determining the temperature of the plasma and normalizing the intensities. The concentration of an atomic species in a sample is determined by calibrating the measured intensity using the emission intensity previously measured for that species, present in a known concentration in a sample for calibration, similar to the unknown sample.

This method has the drawback of requiring a prior calibration for each of the elements of interest. This involves having a set of samples for calibration that are similar to the sample to be analyzed and contain known concentrations for each of the elements of interest. To achieve precise calibrations, the amount of known concentrations for each element must be significant.

To prevent the need of reference samples and prior calibration in the LIBS technique, U.S. Pat. No. 6,657,721 describes a solution based on the existence of local thermodynamic equilibrium (LTE) in the plasma. The temperature of the plasma is obtained from the intensities of emission lines and the spectroscopic data thereof available in the literature. Once the partition functions of all the radiation-emitting species are calculated, the product of their concentration by a common experimental factor is obtained for each element. The elimination of the experimental factor for determining the absolute concentrations is carried out by normalizing each concentration with respect to the sum of all the concentrations.

One drawback of this method is that the temperature and the relative concentrations are obtained under the hypothesis that the spectral lines used are optically thin, the method not including a way to check if this hypothesis is complied with. In fact, this condition is not usually verified in laser-induced plasmas due to their high density, particularly for the intense lines that provide the best precision to the results. Another drawback is that the method is based on the consideration of a homogeneous plasma, particularly with a single temperature value. In reality, laser-induced plasmas are inhomogeneous, having gradients in the characteristic parameters such as temperature, electron density and the densities of the atoms and ions present in the plasma. Taking temperature measurements without spatial resolution, as proposed in this method, means that the values obtained are apparent, population-averaged along the line of sight, resulting in different values for neutral atoms and ions, the emission of which comes from different regions of the plasma. A third drawback of this approach is the absence of a calibration curve or graph which, once known, allows readily obtaining the concentrations of the elements from the measurement of the intensities of spectral lines.

The solution described in application US 2012/0029836 prevents the limitations from the hypothesis of an optically thin and homogeneous plasma by proposing an alternative method for measuring concentrations by means of LIBS technique without prior calibration. To that end, it is based on calculating the absorption coefficient of the plasma for the spectral regions of the lines of interest. The spectral radiance of the plasma is calculated from the absorption coefficient using analytical solutions for the radiative transfer equation. By means of repeatedly comparing the intensity and shape of the spectrum calculated with those of the measured spectrum, the temperature, electron density, the relative elemental concentration values and the width of the plasma are adjusted. The method initially considers a single zone representing a uniform plasma. If, after optimizing the parameters, the difference between the calculated spectrum and the measured spectrum is greater than a predetermined threshold value, the plasma is divided into an increasing number of zones, in steps of three zones, along the direction of observation, characterized by different temperatures and electron densities. The method continues increasing the number of zones until convergence.

One drawback of this method is that it does not contemplate the elimination of spectral lines which, as a result of having a high intensity and/or due to the high concentration of the emitting element in the sample, have a high degree of self-absorption in the plasma, which is hard to describe even with a model with several zones. The inclusion of these lines the spectrum of which is poorly described by the model will reduce the precision of the deduced concentrations. On the other hand, the method includes the determination of the parameters of the plasma and of the elemental concentrations as consecutive steps included in the process. Therefore, it does not allow separating the determination of compositions from the complex method of characterizing the plasma. The absence of a calibration curve or graph is also a drawback of this method.

OBJECT OF THE INVENTION

The present invention relates to an analysis method for analyzing the elemental composition of samples of a solid, liquid or gaseous material from the radiation spectrum emitted by a laser-induced plasma (LIBS technique) which solves the mentioned problems. The method is based on substituting conventional calibration curves and graphs (intensity as a function of concentration) with a different graph (graph Cσ) and a functional relationship (curve Cσ) between the measured line intensity and the concentration of the element in the material. The graphs Cσ include a set of data corresponding to selected spectral lines emitted by the elements of interest. The elemental concentrations and the characteristic parameters of the part of the plasma the radiation of which is detected by the system are deduced by means of fitting the graphs Cσ, using an iterated procedure which compares the experimental graphs with curves calculated in each iteration step. Two different graphs and two different curves Cσ are used, one for the lines of neutral atoms and another for the lines of ions with a unit charge. The calculation of the curves Cσ is made by means of integrating the radiative transfer equation with a model in which the emitting regions of the plasma are divided into zones in order to consider the spatial distributions of the parameters, a model with homogeneous regions applicable when weak lines and/or low concentrations are used also being defined. The characteristic parameters include, for each of the zones of the model, the electron density, the temperature, the product of the total density of atoms and ions by the length along the line of sight and the product of the instrumental factor by the transverse area. The method includes a process of eliminating from the graphs Cσ the data for which the model used is invalid. Three methods are proposed for obtaining the characteristic parameters, one of which is based on samples with a known composition, another method which does not require said samples and a third method which consists of using known characteristic parameters. Once the parameters are obtained, the two curves Cσ calculated from them function as calibration curves for the set of elements of interest.

BRIEF DESCRIPTION OF THE DRAWINGS

For the purpose of aiding to better understand the features of the invention according to a preferred practical embodiment thereof, a set of drawings is attached to the following description in which the following has been depicted with an illustrative character.

DESCRIPTION OF THE INVENTION a) Basic Principles of the LIBS Technique

Figure 1:
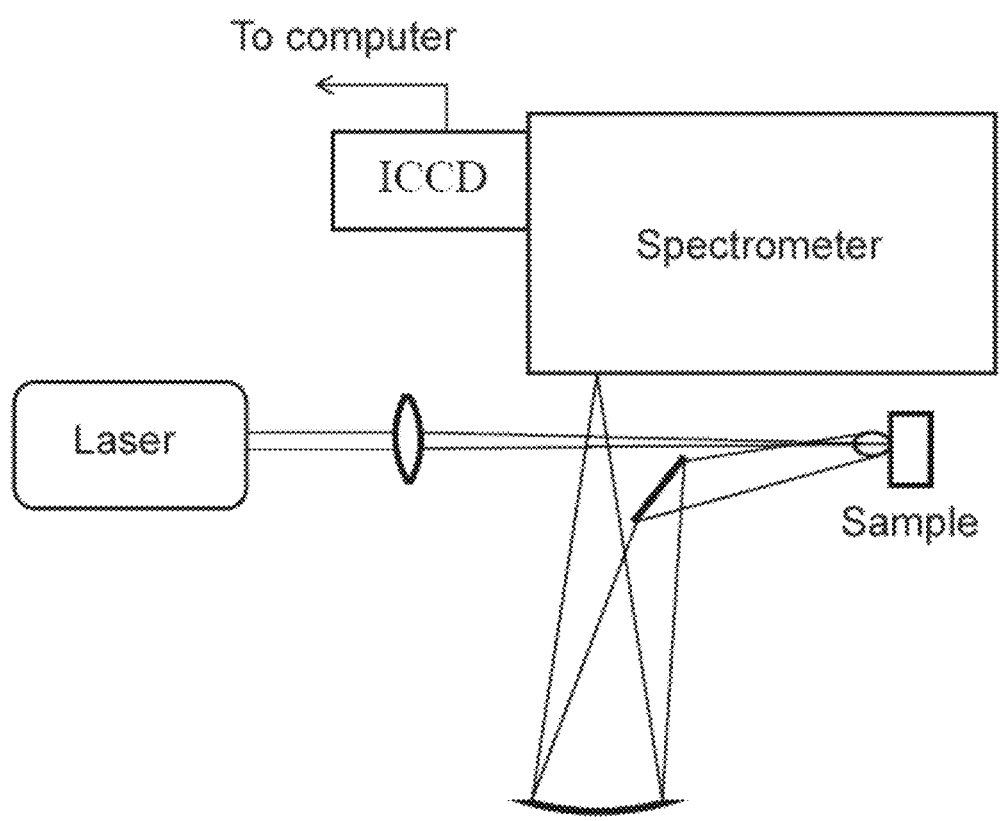
FIG. 1 shows the schematic drawing of the system for composition analysis by means of the method of the invention.

FIG. 1 shows a schematic drawing of the LIBS system used for performing the elemental analysis method proposed in this invention. The LIBS technique uses a pulsed laser focused on a material to generate a plasma. The radiation emitted by a part of the plasma is detected by the system. The LIBS system allows obtaining a radiation spectrum formed by a continuum and the emission lines characteristic of the elements forming the material. The concentrations of the elements are determined by means of analyzing the spectrum.

Various useful relationships are deduced from plasma theory in local thermodynamic equilibrium (LTE). The local temperature T describes in each position the population of the energy levels of the atoms of the plasma by means of the Boltzmann equation. From the population, the emission coefficient for a spectral line emitted by an atom of an element α in an ionization state z is deduced as a function of the atomic data of the transition and of the numerical density of emitters $N_\alpha^z$ $$\varepsilon = \frac{hc}{4\pi\lambda_0} A_{ki} \frac{N_\alpha^z}{U_\alpha^z} g_k e^{-\frac{E_k}{kT}} \qquad (1)$$

where h is the Planck constant, c is the speed of light in vacuum, k is the Boltzmann constant, $A_{ki}$ is the transition probability, $g_k$ and $E_k$ are the degeneration and the energy of the upper level of the transition, $\lambda_0$ is the central wavelength of the transition and $U_\alpha^z = U_\alpha^z(T)$ is the partition function of the emitting species (element α, ionization z). The representation of $\ln[\varepsilon\lambda_0/(A_{ki}g_k)]$ as a function of $E_k$, called a Boltzmann diagram, leads to a straight line with a negative slope $-1/(kT)$, from which the temperature can be obtained.

Furthermore, in LTE, the local temperature value and electron density $N_e$ value determine by means of Saha equation the relationship between the numerical densities of species in consecutive ionization states $$S^{10} = \frac{N_\alpha^1}{N_\alpha^0} = \frac{2U_\alpha^1}{N_e U_\alpha^0} \left(\frac{mkT}{2\pi\hbar^2}\right)^{3/2} \exp\left(-\frac{E_\infty^0 - \Delta E_\infty^0}{kT}\right) \qquad (2)$$

where $\hbar = h/2\pi$, m is the mass of the electron, $E_\infty^0$ is the ionization energy and $\Delta E_\infty^0$ is the correction thereof due to interactions in the plasma.

Finally, the existence of LTE allows using the radiative transfer equation, the integration of which leads to the following expression for the spectral intensity emitted by a plasma element having a section transverse to the line of sight A and a length l along the line of sight $$I(\lambda) = A \int_0^l L_P(\lambda,x) k'(\lambda,x) e^{-\int_x^l k'(\lambda,x')dx'} dx \qquad (3)$$

where $L_p(\lambda,x)$ is the Planck radiance for a black body and $k'(\lambda,x)$ is the effective absorption coefficient for a position x along the line of sight. The latter can be obtained by means of the expression $$k'(\lambda,x) = k_t(x) N_\alpha^z(x) V(\lambda,x) \qquad (4)$$

where $V(\lambda)$ is the line profile, given by a normalized Voigt profile of Doppler width $\Delta\lambda_D$ and Lorentzian width $\Delta\lambda_L$, and the coefficient $k_t$, dependent on the atomic data of the transition and on the temperature, has been defined by means of $$k_t = \frac{e^2 \lambda_0^2}{4\varepsilon_0 mc^2} f \frac{g_i e^{-\frac{E_i}{kT}}}{U} \left(1 - e^{-\frac{E_k - E_i}{kT}}\right) \qquad (5)$$

where $\varepsilon_0$ is the permittivity of vacuum, $g_i$ and $E_i$ the degeneration and the energy of the lower level and f the oscillator strength.

The intensity detected for a spectral line emitted by the plasma element is obtained by integration of the spectral intensity $$I = \beta \int_{line} I(\lambda) d\lambda \qquad (6)$$

where $\beta$ is the instrumental factor of the system defined as the number of counts obtained per watt of gathered radiation.

In the case of a homogeneous plasma, after integrating equation (3), equation (6) becomes $$I = \beta A L_P \int_{line} (1 - e^{-\tau(\lambda)}) d\lambda \qquad (7)$$

where $L_P = L_P(\lambda_0)$ and $\tau(\lambda)$ is the optical depth, given by $$\tau(\lambda) = k'(\lambda) l = k_t N_\alpha^z l V(\lambda) \qquad (8)$$

Due to the high electron density in laser-induced plasmas, it can generally be assumed that the main broadening mechanism for broadening the spectral lines is the Stark effect. As a result, the Lorentzian width of a spectral line can be obtained from the electron density $N_e$ if its Stark width is known. In turn, the electron density in the plasma can be determined from the measurement in the experimental spectrum of the Lorentzian width of a line the Stark width of which is known and large enough.

It is important to highlight that the temperature appearing in equations (1) and (2) is the local temperature in the plasma. When the temperature is determined by means of Boltzmann diagrams constructed from the line intensity measured with spatial integration as is customary in the LIBS technique, a temperature value resulting from an average weighed by the emission coefficient within the region from which the emission of the spectrum occurs, is obtained. Particularly, the temperature measured with lines of neutral atom is different from that obtained from lines of ions with a unit charge, given that the two ionization states occupy different regions of the plasma. The same occurs with electron density, (or the Lorentzian width related therewith) when it is obtained from the experimental profile measured with spatial integration.

b) Description of the Composition Analysis Method Object of the Invention b1) Defining the Curves and Graphs Cσ

To introduce the new functional relationship between the line intensities and the concentrations in the material, a homogeneous plasma model is first considered.

By assuming that the laser-induced plasma is only formed by neutral atoms and ions with a unit charge, the numerical density of an element α in the plasma will be $$N_\alpha = N_\alpha^0 + N_\alpha^1 \qquad (9)$$

where $N_\alpha^0$ and $N_\alpha^1$ are the densities of neutral atoms and ions with a unit charge, respectively. By assuming that the stoichiometry in the ablation process is maintained, such that it is the same in the plasma as in the material, the following relationship is met $$C = 10^2 \frac{N_\alpha}{N} \qquad (10)$$

where N is the total density, including atoms and ions with a unit charge for all the elements in the plasma and C is the concentration of the element in the material expressed in atomic percentage (at. %). It is deduced from equations (2) and (9) that the densities of neutral atoms and ions in the plasma can be expressed as $$N_\alpha^z = r_i N_\alpha \qquad (11)$$

where $r_i$ is an ionization factor defined as follows:

$$r_i = \frac{1}{1 + S^{10}} \text{ for neutral atoms} \qquad (12)$$

$$r_i = \frac{1}{1 + \frac{1}{S^{10}}} \text{ for ions with a unit charge} \qquad (13)$$

By substituting equations (10) and (11) into equation (8), the optical depth can be expressed as $$\tau(\lambda) = 10^{-2} C N l k_t r_i V(\Delta) \qquad (14)$$

A line optical depth is defined as averaging at the line profile by means of the expression $$\tau_l = \frac{1}{\Delta \lambda_L} \int_{line} \tau(\lambda) d\lambda = 10^{-2} C N l k_t r_i \frac{1}{\Delta \lambda_L} \qquad (15)$$

and a line cross section by means of $$\sigma_l = \frac{k_t r_i}{\Delta \lambda_L} \qquad (16)$$

The relationship between the amounts $\tau_l$ and $\sigma_l$ is as follows $$\tau_l = 10^2 C N l \sigma_l \qquad (17)$$

Using the equation (14) for optical depth and the definition of $\sigma_l$ given by equation (16), equation (7) provides a functional relationship, called curve Cσ, between the intensity of a line and the concentration of the emitting element in the material which is valid for all the elements and which can be expressed in the compact form as $$\frac{I}{L_P \Delta \lambda_L} = f(10^{-2} C \sigma_l) \qquad (18)$$

In the small optical depth limit ($C\sigma_l \to 0$), this expression tends towards a linear relationship $$\frac{I}{L_P \Delta \lambda_L} = \beta A N l 10^{-2} C \sigma_l \qquad (19)$$

Figure 2:
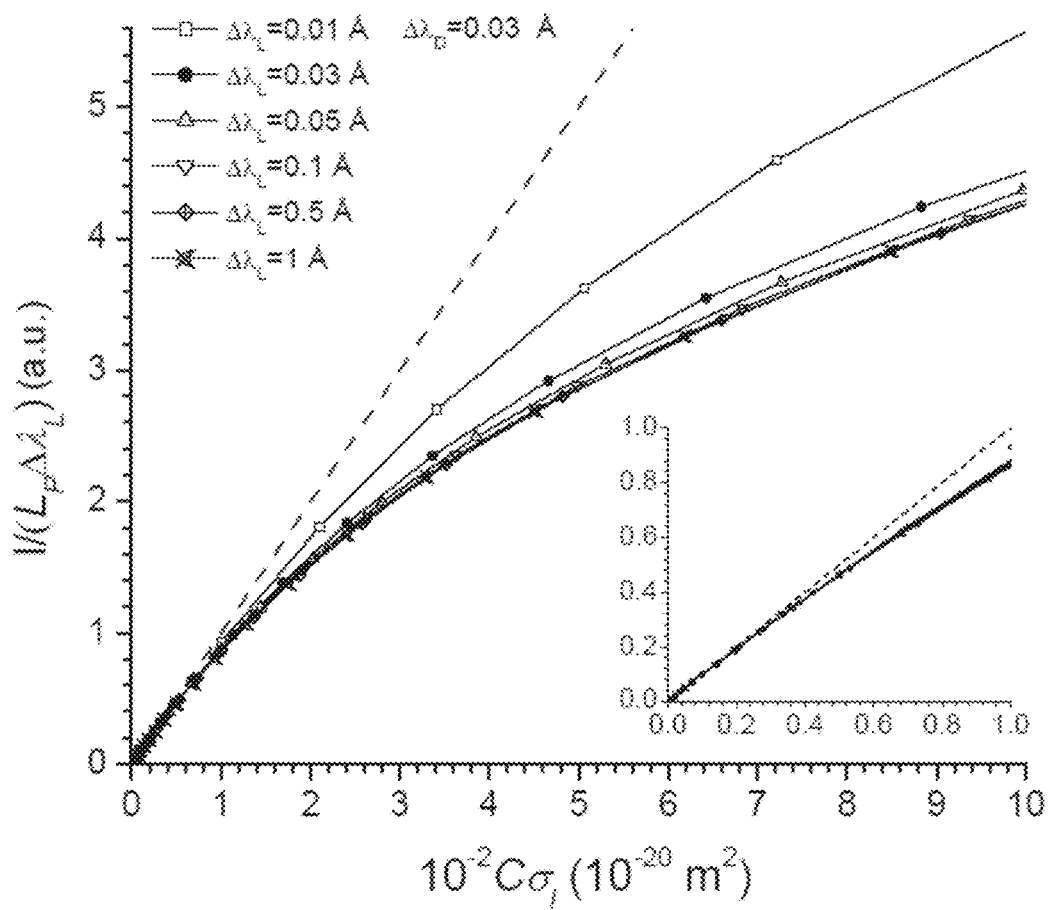
FIG. 2 shows the graph representation of the functional relationship between the emission intensity of a spectral line and the concentration of the emitting element in the material (curve Cσ).

The curve Cσ given by equation (18) depends on parameters $N_e$, T, Nl and βA. It can be calculated by numerical integration according to equation (7) from the Voigt profile $V(\lambda)$ and can be depicted graphically. FIG. 2 shows said curves calculated for a typical Doppler width $\Delta\lambda_D = 0.03$ Å and Lorentzian widths $\Delta\lambda_L$ in a range from 0.01 Å to 1 Å. $L_P = 1$, $\beta A N l = 1$ and typical values of $C\sigma_l$ were used in this graph. As can be seen, except for the case of a small Lorentzian width in the order of 0.01 Å, which is rather uncommon in laser-induced plasmas, the curves are very close, tending towards the same linear relationship, given by equation (19), in the small optical depth limit.

The existence of a curve Cσ which is similar for lines having a different Lorentzian width (given a certain Doppler width) for optical depth values close to the optically thin limit, suggests the construction of a graph from the experimental data with $I/(L_P \Delta\lambda_L)$ in the y-axis and $10^{-2}C\sigma_l$ in the x-axis, called a Cσ graph.

The analysis method object of this invention includes obtaining the characteristic parameters of the part of the plasma the radiation of which is detected by the system. Methods called characterization methods which allow obtaining said parameters from the detected spectra using the graphs and curves Cσ are proposed.

b2) Inhomogeneous Plasma Model

By obtaining the parameters of the plasma from spectra measurements made with spatial integration and by using the curves Cσ defined in equation (18) and calculated by means of a homogeneous model through equations (7) and (14), the parameters $N_e$, T, Nl and βA that are deduced are different for lines of neutral atoms and ions. That is because, in reality, the plasma is an inhomogeneous medium and the line emission of the two ionization states comes from different regions of the plasma. Therefore, in the description that follows, it is necessary to consider two graphs and curves Cσ individually, one for the emitting region of the lines of neutral atoms and another for the emitting region of the lines of ions with a unit charge. The parameters for neutral atoms will be designated with superscript z=0, and the parameters for ions will be designated with z=1.

Figure 3:
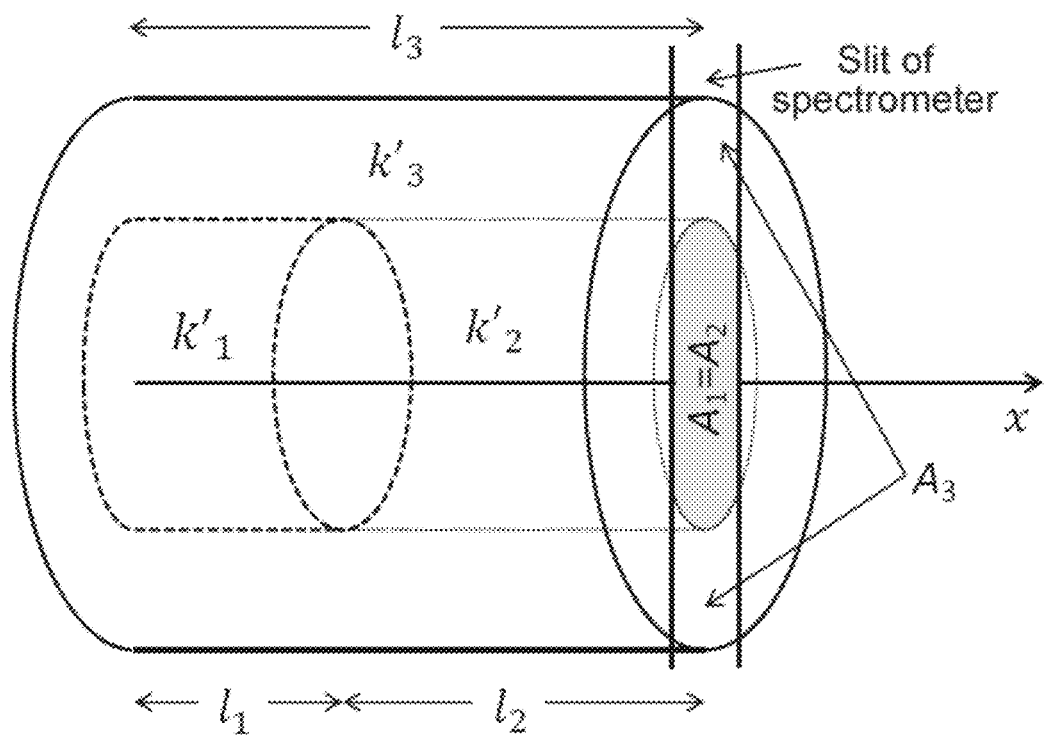
FIG. 3 shows the example of a model for describing the inhomogeneity of the plasma.

To describe the inhomogeneous plasma, a model is constructed representing the spatial distributions of electron density, temperature and total density of atoms and ions in the emitting regions of the plasma corresponding to neutral atoms and ions with a unit charge. In this model, the emitting region is divided into elements, each with a certain area transverse to the line of sight or direction of propagation of the radiation from the plasma to the component of the LIBS system gathering said radiation. These elements are in turn divided into zones along the line of sight. Within each of these zones, the parameters of the plasma are assumed to be homogeneous and there is a certain value of effective absorption coefficient (4). FIG. 3 shows an example of an inhomogeneous model formed by two elements, one inner element comprising two zones having coefficients $k'_1$ and $k'_2$, lengths $l_1$ and $l_2$ and identical areas $A_1=A_2$, which is surrounded by another outer element with a single zone having coefficient $k'_3$, length $l_3=l_1+l_2$ and area $A_3$. Said figure also depicts the part of the emitting region of the plasma the radiation of which is gathered by the slit of the spectrometer and therefore detected by the LIBS system in the configuration of FIG. 1. The part of the plasma the emission of which is detected can be different if the configuration of the system changes, for example, if a fiber optic cable is used for gathering the plasma radiation. Since the emitting regions of neutral atoms and ions are individually described in this inhomogeneous model, for defining the geometry of the model, the lengths $l_j^z$ and the transverse areas $A_j^z$ are used, where the subscript j defines the zones and the superscript is z=0 for the emitting region of the lines of neutral atom and z=1 for the lines of ions.

Given a model, in order to obtain the curve Cσ (18) corresponding to one of the emitting regions, either for the lines of neutral atoms or for the lines of ions, the spatial integral along the line of sight of the radiative transfer equation, given by equation (3), is first calculated for each plasma element of said region. The spectral intensity resulting from the integration with the inhomogeneous model depends on the optical depths $\tau_j^z = k'^z_j l_j^z$ of the different zones, so, like in the homogeneous model [equation (14)], the total density $N_j^z$ in each zone is multiplied by the length $l_j^z$, in the form of a single parameter $(Nl)_j^z$. Likewise, a parameter $(\beta A)_j^z$ including the transverse area of each zone and the instrumental factor, is considered in each zone. The line intensity is obtained by integrating in wavelengths the spectral intensity according to equation (6), summing up the result for all the elements of the emitting region.

It is deduced from the preceding description that the set of parameters necessary for calculating the curve Cσ with the inhomogeneous model comprises the electron densities $N_{e,j}^z$, temperatures $T_j^z$, and the parameters $(Nl)_j^z$ and $(\beta A)_j^z$. To better describe the actual distribution of parameters in the plasma, a model with more zones can be used even though this obviously increases the number of parameters.

Curves Cσ for the inhomogeneous model tend towards those obtained for a homogeneous model when the product $\tau_l \Delta\lambda_L \to 0$. As a result, in order for the curves Cσ for the inhomogeneous model to coincide in a single curve in the optically thin limit, when obtaining the x-axis and y-axis of the graphs Cσ (18), the amounts $\sigma_l$, $L_P$ and $\Delta\lambda_L$ are calculated for the temperature and electron density values deduced from the application of the homogeneous model, similarly to the amount $\tau_l \Delta\lambda_L$ used for evaluating the validity of the model. The more realistic the distribution of parameters used in the inhomogeneous model is, the greater the limit value of $\tau_l \Delta\lambda_L$ compatible with the validity of the model can be considered.

b3) Steps of the Method

Figure 4:
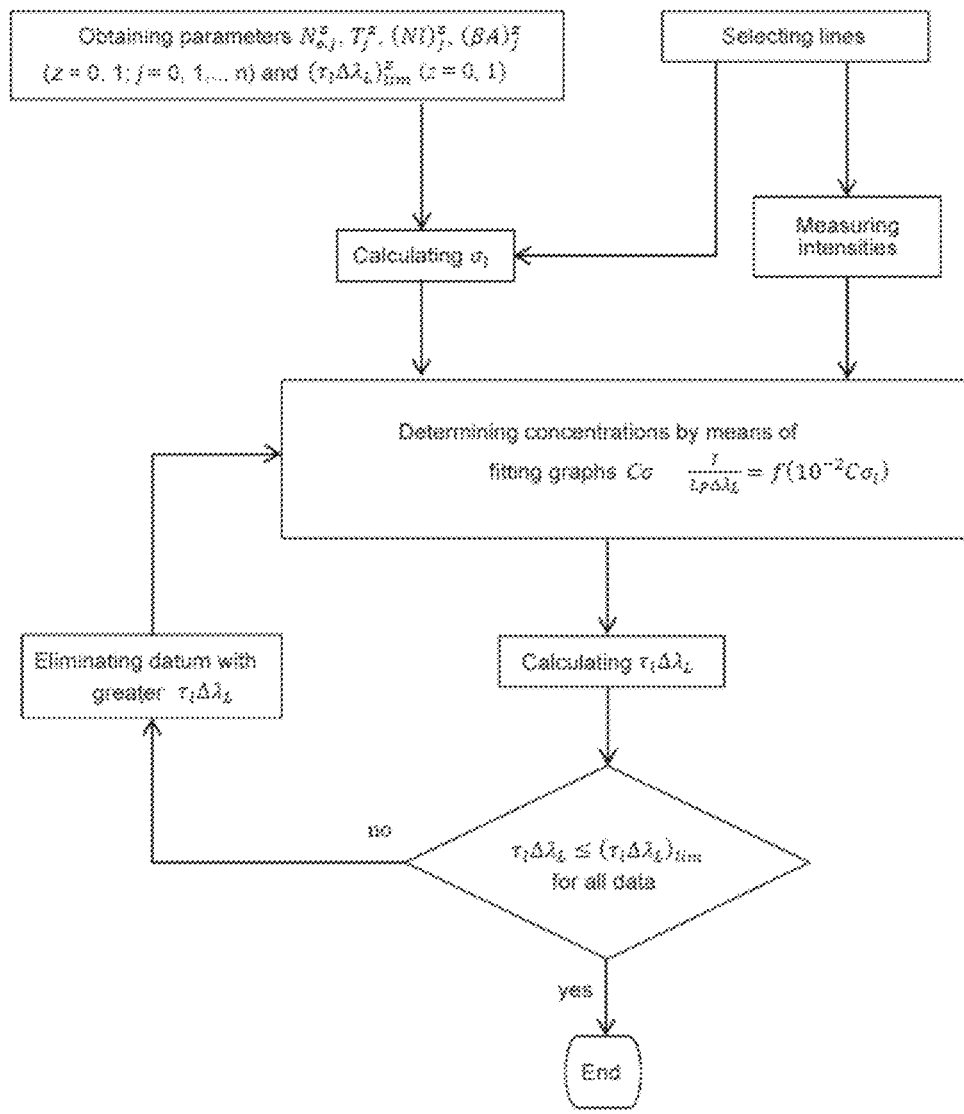
FIG. 4 shows the flow diagram of the analysis method.

The proposed method is based on fitting the graphs Cσ for the emitting regions of neutral atoms and ions with a unit charge, constructed from the data of intensities measured for a set of selected spectral lines. To perform the fitting, the measured graphs Cσ are compared with the calculated curves Cσ in an iterative process. The steps are described in detail below:

The analysis method, the flow diagram of which is shown in FIG. 4, has as a result the elemental composition of the samples of a material. The process starts with obtaining the characteristic parameters of the part of the plasma the radiation of which is detected by the system, including parameters $N_{e,j}^z$, $T_j^z$, $(Nl)_j^z$ and $(\beta A)_j^z$.(z=0, 1; j=0, 1, ..., n), as well as obtaining the limit value $(\tau_l \Delta\lambda_L)_{lim}^z$ which determines the validity of the inhomogeneous model of n zones. The superscript is z=0 for the emitting region of the lines of neutral atom and z=1 for the lines of ions, whereas the subscript j=0 has been defined for the values obtained with the homogeneous model, and j=1, ..., n for the values corresponding to the inhomogenous model of n zones. The mentioned parameters and limit value are obtained by three alternative methods described below.

Spectral lines of atoms and ions of the elements of interest are selected, obtaining their atomic data for calculating the line crosssection $\sigma_l$ in the following step by means of equation (16), using the temperature $T_0^z$ and electron density $N_{e,0}^z$ in the calculation. After measuring the intensities of the selected lines, two graphs Cσ are constructed, one for neutral atoms and another for ions, introducing an initial arbitrary value of concentrations. A process of fitting by means of an iterative algorithm which compares said graphs with curves Cσ. The calculation of the curves is performed by means of equation (18), where the intensity is determined by integrating in wavelengths the spectral intensities obtained by means of the spatial integration of the radiation transfer equation, according to equation (3). The characteristic parameters obtained in the first step of the process, defined for a model of n zones, are used in this calculation. The fitting process provides the concentrations of the elements when the iteration ends.

The method continues with the elimination of data from the graphs $C\sigma$ which, due to the lack of validity of the model of n zones used for determining the intensity for that datum, negatively affect the precision of the obtained concentrations. To that end, the line optical depth is calculated for each datum according to equation (17) by introducing the concentrations resulting from the preceding fitting. The following condition for the validity of the plasma model used is then evaluated for all the data $$\tau_l \Delta \lambda_L \leq (\tau_l \Delta \lambda_L)_{lim} \tag{20}$$

where $(\tau_l \Delta \lambda_L)_{lim}$ is the limit value for which the model is valid. If said condition is not complied with for all the data, the datum for which the amount $\tau_l \Delta \lambda_L$ is greater is eliminated from the process. After the elimination of the datum, the fitting is again performed, an iterated process which ends when all the data comply with the condition (20) being developed. The concentrations of the elements in the material are obtained when the process ends.

Three alternative methods described below are proposed for obtaining the characteristic parameters in the first step of the analysis method.

1. Characterization Using Standard Samples

Figure 5:
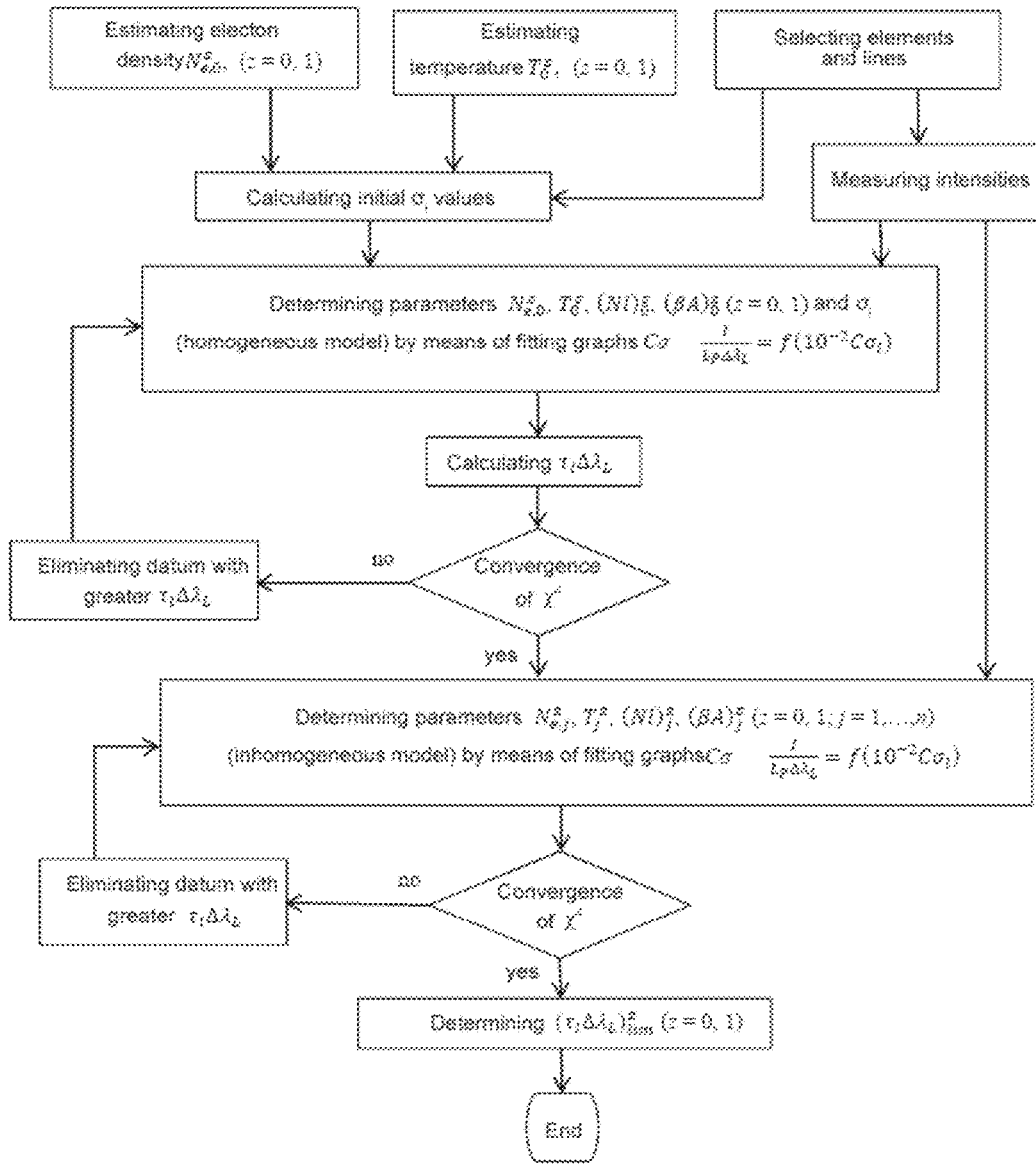
FIG. 5 shows the flow diagram of the characterization method using standard samples.

This method, the flow diagram of which is shown in FIG. 5, can be used in the case of having at least one sample with at least one element with a known concentration, known as a standard sample.

It starts by selecting, from the spectra obtained for the standard samples, elements present in the samples for which a set of spectral lines of neutral atoms and ions the atomic data of which are known is detected, which lines are selected for characterization, obtaining their atomic data. The initial values of the parameters $N_{e,0}{}^z$, $T_o{}^z$ (z=0, 1) are estimated. This estimation can be made by the Stark broadening-based method for electron density $N_{e,0}{}^z$ and by means of Boltzmann diagram method for temperature $T_o{}^z$.

The next step is calculating the initial line crosssection $\sigma_l$ values defined in equation (16) by introducing the estimated temperature and electron density in the calculation. After measuring the intensities of the selected lines for the different samples, two graphs $C\sigma$ are constructed, one for neutral atoms and another for ions, using the selected lines and concentrations of elements, and introducing the initial line crosssection $\sigma_l$ values. A fitting process similar to that used in the analysis method is then carried out, with the difference that in this case the fitting provides the parameters $N_{e,0}{}^z$, $T_o{}^z$, $(Nl)_0{}^z$, $(\beta A)_0{}^z$ (z=0, 1), as well as new line crosssection $\sigma_l$ values when the iteration ends. In the fitting process, the calculation of the curves $C\sigma$ is performed with a homogeneous model, calculating the intensities by means of equations (7) and (14).

The method continues with an elimination process performed for each of the two graphs $C\sigma$ of the data which, due to the lack of validity of the homogeneous model, negatively affect the precision of the obtained parameters. To that end, the line optical depth is calculated for each datum according to equation (17), introducing the line crosssection resulting from the preceding fitting and the concentration of the element. The fitting of the graph $C\sigma$ performed results in a chi-square value ($\chi^2$) of the fitting. An iterated process eliminating the datum for which the amount $\tau_l \Delta \lambda_L$ is greater is started. After eliminating the datum, the fitting is again performed, resulting in a new value of $\chi^2$. The iterated data elimination process continues until achieving the convergence of $\chi^2$. The final value of the parameters for the homogeneous model, as well as the final line crosssection $\sigma_l$ values are obtained when the process ends.

In order for the parameters to be as similar as possible to the actual parameters, which allows including data having greater value for the amount $\tau_l \Delta \lambda_L$ in the graphs $C\sigma$, an inhomogeneous plasma model is then considered. With this model, the steps of fitting the graphs $C\sigma$ and of eliminating data described in the preceding paragraphs are repeated, resulting in parameters $N_{e,j}{}^z$, $T_j{}^z$, $(Nl)_j{}^z$ and $(\beta A)_j{}^z$ (j=1, ..., n) corresponding to the n zones of the model. The limit value $(\tau_l \Delta \lambda_L)_{lim}$ for the validity of the inhomogenous model of n zones is obtained after the iterated data elimination process ends.

2. Characterization without Using Standard Samples

Figure 6:
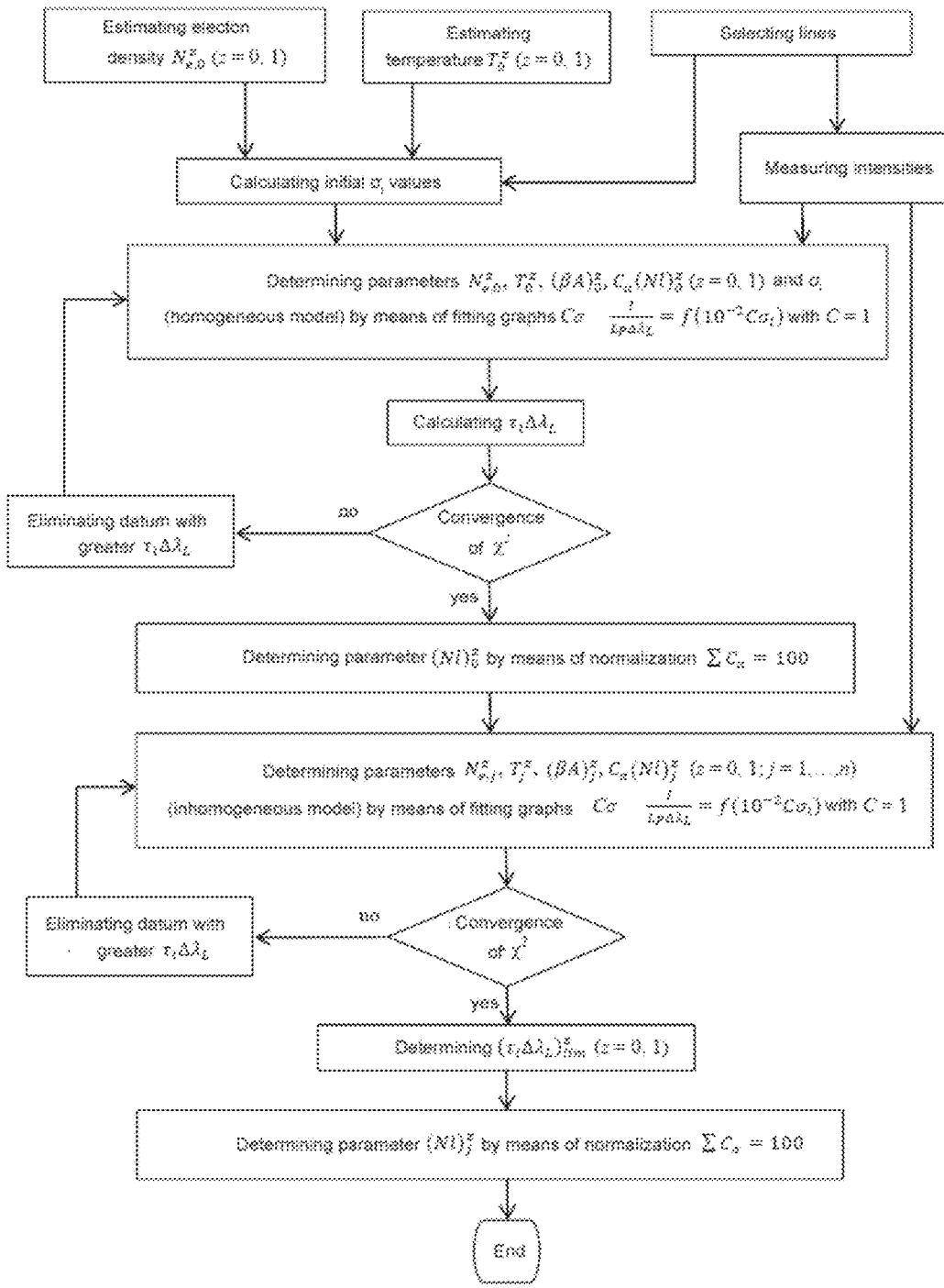
FIG. 6 shows the flow diagram of the characterization method without using standard samples.

This method, the flow diagram of which is shown in FIG. 6, uses a sample of the material of interest, the composition of which is unknown. The process is similar to characterization using standard samples, with some differences that are described below.

The method starts by selecting spectral lines from the spectrum obtained for the sample used. In this case, the set of selected lines must include all the elements a for which lines are detected in the spectrum. The atomic data of the selected lines are obtained. The initial estimation of the electron density $N_{e,0}{}^z$ and temperature $T_o{}^z$ is then performed either by means of Stark broadening for electron density and by means of the Boltzmann diagram method for temperature.

After calculating the initial line crosssection $\sigma_l$ values and measuring the intensities of selected lines, two graphs $C\sigma$ are constructed in which in this case the x-axis is defined with C=1. The fitting process with a homogeneous model is then carried out, parameters $N_{e,0}{}^z$, $T_0{}^z$, $(\beta A)_0{}^z$, as well as the product $C_\alpha(Nl)_0{}^z$ of the concentration of the element $\alpha$ by the parameter $(Nl)_0{}^z$ and the new line cross $\sigma_l$ values, resulting from the fitting.

The method continues with the calculation of the amounts $\tau_l \Delta \lambda_L$ and the iterative data elimination process, resulting in the final values of the parameters $N_{e,0}{}^z$, $T_0{}^z$, $(\beta A)_0{}^z$ and the product $C_\alpha(Nl)_0{}^z$. To obtain the parameter $(Nl)_0{}^z$, a concentration normalization, given by the following equation is performed $$\sum_\alpha C_\alpha = 100 \tag{21}$$

from which the following is deduced $$(Nl)_0^z = 10^{-2} \sum_\alpha [C_\alpha(Nl)_0^z] \tag{22}$$

The fitting and data elimination process is now performed with the inhomogeneous model, providing parameters $N_{e,j}{}^z$, $T_j{}^z$, $(\beta A)_j{}^z$, as well as the product $C_\alpha(Nl)_j{}^z$ (j=1, ..., n). The limit value $(\tau_l \Delta \lambda_L)_{lim}$ for which the inhomogeneous model of n zones is valid is obtained after the iterated data elimination process ends. In this case, the application of normalization (21) allows determining the parameter $(Nl)_j^z$, which turns out to be $$(Nl)_j^z = 10^{-2} \sum_\alpha [C_\alpha (Nl)_j^z] \quad (23)$$

3. Use of Known Characteristic Parameters

If the characteristic parameters $N_{e,j}^z$, $T_j^z$, $(Nl)_j^z$ and $(\beta A)_j^z$ (j=0, 1, . . . , n), as well as the limit value $(\tau_l \Delta \lambda_L)_{lim}^z$ (z=0, 1) are known because a prior characterization has been performed, for example, these values can be taken in the first step of the analysis method.

The invention claimed is:

1. Quantitative analysis method for analyzing the elemental composition of materials by means of laser-induced breakdown spectroscopy, known as LIBS technique, in which the concentrations of the elements making up a set of samples of materials from which a radiation-emitting laser-induced plasma can be generated are determined, where the method comprises the following steps:
   1. a step of obtaining the characteristic parameters of the part of the plasma the radiation of which is detected by the system, said parameters including electron density $N_{e,j}^z$, temperature $T_j^z$, the product $(Nl)_j^z$ of the total density N, including atoms and ions with a unit charge for all the elements present in the sample, by length l along the line of sight and the product $(\beta A)_j^z$ of area A transverse to the line of sight by the instrumental factor $\beta$ of the system, defined as the number of counts obtained per watt of gathered radiation, the values of the parameters being defined for different values of the scripts (j, z), the script z taking the values z=0 for the emitting region of neutral atom lines and z=1 for the emitting region of ions with a unit charge, the script j taking the values j=0, 1, . . . , n, the script j=0 corresponding to a plasma model called a homogeneous plasma model, in which the emitting regions of neutral atom lines and ions with a unit charge are considered homogeneous and the values j=1, . . . , n corresponding to a model called an inhomogeneous model, in which the emitting regions of neutral atom lines and ions with a unit charge are divided into an n number of zones, each of them considered homogeneous, the subscript j defining the value of the parameter in each zone, the limit value for the validity of the inhomogeneous model of n zones $(\tau_l \Delta \lambda_L)_{lim}^z$ also being obtained, with z=0, 1, of the product $\tau_l \Delta \lambda_L$, where $\tau_l$ is the line optical depth, defined by $$\tau_l = 10^{-2} C(Nl)_0^z \sigma_l$$

where C is the concentration of the element in the material expressed in atomic percentage (at. %), where $\sigma_l$ is the line cross-section, given by the equation $$\sigma_l = \frac{k_t r_i}{\Delta \lambda_L}$$

where $\Delta \lambda_L$ is the Lorentzian width of the line, determined by multiplying the Stark width w by the electron density $N_{e,0}^z$, where $k_t$ is $$k_t = \frac{e^2 \lambda_0^2}{4\varepsilon_0 m c^2} f \frac{g_i e^{-\frac{E_i}{kT}}}{U} \left(1 - e^{-\frac{E_k - E_i}{kT}}\right)$$

where e is the elemental charge, $\varepsilon_0$ is the permittivity of vacuum, m is the mass of the electron, k is the Boltzmann constant, $\lambda_0$ is the central wavelength of the transition, $g_i$ is the degeneration of the lower level, $E_i$ and $E_k$ are the energies of the lower and upper levels, f is the oscillator strength, U is the partition function of the emitting species and $r_i$ is the ionization factor, defined as follows $$r_i = \frac{1}{1 + S^{10}} \text{ for neutral atoms}$$

$$r_i = \frac{1}{1 + \frac{1}{S^{10}}} \text{ for ions with a unit charge}$$

where $S^{10}$ is the relationship, given by Saha equation, between the density of ions with a unit charge and the density of neutral atoms;

2. a step selecting spectral lines of neutral atoms and ions with a unit charge of the elements of interest, obtaining their atomic data, including $\lambda_0$, $g_i$, $E_i$, $E_k$, f and w;

3. a step of calculating the line cross-sections $\sigma_l$ for the lines selected in the preceding step, the temperature $T_0^z$ and the electron density $N_{e,0}^z$ being used in the calculation;

4. a step of measuring the intensities I of the spectral lines selected in step 2;

5. a step of determining the concentrations C of the elements of interest by means of fitting two graphs $C\sigma$, one for neutral atoms and another for ions with a unit charge, which are constructed using the line cross-sections $\sigma_l$ calculated in step 3, the graphs $C\sigma$ defined as graphs with $I/(L_P \Delta \lambda_L)$ in the y-axis, where $L_P = L_P(\lambda_0)$ is the Planck radiance for a black body calculated for the temperature $T_0^z$, and $10^{-2} C \sigma_l$ in the x-axis, where C is the concentration of the element in the material expressed in atomic percentage (at. %), introducing initial arbitrary concentration values and using to perform the fitting an iterative algorithm which compares the experimental graphs with the curves $C\sigma$, defined for neutral atoms and for ions with a unit charge as functional relationships in the form of $$\frac{I}{L_P \Delta \lambda_L} = f(10^{-2} C \sigma_i),$$

$I/(L_P \Delta \lambda_L)$ being calculated by integrating in wavelengths the spectral intensities obtained by means of the spatial integration of the radiation transfer equation with the parameters of the inhomogeneous model of n zones j=1, . . . , n obtained in step 1;

6. a step of calculating, for the data of the graphs $C\sigma$ resulting from the preceding step, the products $\tau_l \Delta \lambda_L$, the concentrations C resulting from the preceding step and the parameters obtained in step 1 being used in the calculation of $\tau_l$;

7. a step of evaluating, for the data of each of the two graphs $C\sigma$, a condition on the validity limit of the plasma model, given by:

$$\tau_l \Delta\lambda_L \leq (\tau_l \Delta\lambda_L)_{lim}^z \qquad 5$$

where $(\tau_l \Delta\lambda_L)_{lim}^z$ is the limit value determined in step 1 for which the inhomogeneous model of n zones used is valid, the datum for which the amount $\tau_l \Delta\lambda_L$ is greater being eliminated if the condition is not complied with;

8. repeating steps 5 to 7 until all data comply with the condition described in step 7.

2. Method according to claim 1, where in the case of having at least one sample with at least one element with a known concentration, step 1 is performed by means of a process called characterization with standard samples, comprising the following steps:

a) a step of selecting one or several elements with a known concentration present in one or several of the available samples and of selecting the spectral lines of neutral atoms and ions with a unit charge of said elements, obtaining their atomic data;

b) a step of estimating an initial electron density value $N_{e,0}^z$ ($z=0, 1$);

c) a step of estimating an initial temperature value $T_0^z$ ($z=0, 1$);

d) a step of calculating the initial line cross-section $\sigma_l$ values for the lines selected in step a);

e) a step of measuring the intensities of the spectral lines selected in step a);

f) a step of determining the parameters $N_{e,0}^z$, $T_0^z$, $(Nl)_0^z$ and $(\beta A)_0^z$ ($z=0, 1$) by means of fitting two graphs $C\sigma$, one for neutral atoms and another for ions with a unit charge, which are constructed using the lines and concentrations of elements selected in step a) and introducing the initial line cross-section $\sigma_l$ values resulting from step d), using to perform the fitting an iterative algorithm which compares the experimental graphs with the curves $C\sigma$ calculated with a homogeneous plasma model, new line cross-section a values being obtained when the iteration ends;

g) a step of calculating, for each of the initial data of the graphs $C\sigma$ from preceding step, the amounts $\tau_l \Delta\lambda_L$, the parameters resulting from the preceding step being used in the calculation;

h) a step of evaluating the convergence of chi-square value ($\chi^2$) resulting from each of the fittings of step f) and, if convergence does not occur, a step of eliminating for each graph $C\sigma$ the datum for which the amount $\tau_l \Delta\lambda_L$ is greater;

i) repeating steps f) to h) until the convergence of $\chi^2$;

j) a step of determining the parameters $N_{e,j}^z$, $T_j^z$, $(Nl)_j^z$ and $(\beta A)_j^z$ ($z=0, 1; j=1, \ldots, n$) by means of fitting two graphs $C\sigma$, one for neutral atoms and another for ions with a unit charge, which are constructed using the lines and concentrations of elements selected in step a) and introducing the line cross-section $\sigma_l$ values resulting from the preceding step, using to perform the fitting an iterative algorithm which compares the experimental graphs with the curves $C\sigma$ calculated with an inhomogeneous plasma model;

k) a step of evaluating the convergence of the chi-square value ($\chi^2$) resulting from each of the fittings of step j) and, if convergence does not occur, a step of eliminating for each graph $C\sigma$ the datum for which the amount $\tau_l \Delta\lambda_L$ is greater;

l) repeating steps j) and k), until all data comply with the condition established in step k);

m) a step of determining the limit value $(\tau_l \Delta\lambda_L)_{lim}^z$ ($z=0, 1$) defined from each graph $C\sigma$ resulting from the preceding step as the product $\tau_l \Delta\lambda_L$ calculated for the datum for which said product is greater.

3. Method according to claim 1, where in the case of not having any sample which contains at least one element with a known concentration, step 1 is performed by means of a process called characterization without standard samples, comprising the following steps:

a) a step of selecting spectral lines of neutral atoms and ions with a unit charge of the elements present in a sample, obtaining their atomic data;

b) a step of estimating an initial electron density value $N_{e,0}^z$ ($z=0, 1$);

c) a step of estimating an initial temperature value $T_0^z$ ($z=0, 1$);

d) a step of calculating the initial line cross-section $\sigma_l$ values for the lines selected in step a);

e) a step of measuring the intensities of the spectral lines selected in step a);

f) a step of determining the parameters $N_{e,0}^z$, $T_0^z$, $(\beta A)_0^z$, as well as the product $C_\alpha(Nl)_0^z$ ($z=0, 1$), by means of fitting two graphs $C\sigma$ with $C=1$, one for neutral atoms and another for ions with a unit charge, which are constructed using the lines selected in step a), introducing the initial line cross-section $\sigma_l$ values resulting from step d), using to perform the fitting an iterative algorithm which compares the experimental graphs with the curves $C\sigma$ calculated with a homogeneous plasma model, new line cross section $\sigma_l$ values being obtained when the iteration ends;

g) a step of calculating, for each of the initial data of the graphs $C\sigma$ from the preceding step, the amounts $\tau_l \Delta\lambda_L$, the parameters resulting from the preceding step being used in the calculation;

h) a step of evaluating the convergence of the chi-square value ($\chi^2$) resulting from each of the fittings of step f) and, if convergence does not occur, a step of eliminating for each graph $C\sigma$ the datum for which the amount $\tau_l \Delta\lambda_L$ is greater;

i) repeating steps f) to h), until the condition established in step h) is complied with;

j) a step of normalizing, in which the sum of concentrations for all the elements with a significant concentration in the sample must be equal to 100, resulting in parameter $(Nl)_0^z$;

k) a step of determining the parameters $N_{e,j}^z$, $T_j^z$, $(\beta A)_j^z$, as well as the product $C_\alpha(Nl)_j^z$ ($z=0, 1; j=1, \ldots, n$), by means of fitting two graphs $C\sigma$ with $C=1$, one for neutral atoms and another for ions with a unit charge, which are constructed using the lines and concentrations of elements selected in step a) and introducing the line cross-section $\sigma_l$ values resulting from step i), using to perform the fitting an iterative algorithm which compares the experimental graphs with the curves $C\sigma$, calculated with an inhomogeneous plasma model;

l) a step of evaluating the convergence of the chi-square value ($\chi^2$) resulting from each of the fittings of step k) and, if convergence does not occur, a step of eliminating for each graph $C\sigma$ the datum for which the amount $\tau_l \Delta\lambda_L$ is greater;

m) repeating steps k) and l), until the condition established in step l) is complied with;

n) a step of determining the limit value $(\tau_l \Delta \lambda_L)_{lim}^z$ (z=0, 1) defined from each graph Cσ resulting from the preceding step as the product $\tau_l \Delta \lambda_L$ calculated for the datum for which said product is greater;

o) a step of normalizing, in which the sum of concentrations for all the elements with a significant concentration in the sample must be equal to 100, resulting in parameter $(Nl)_j^z$ (z=0, 1; j=1, ..., n).

4. Method according to claim 1, where in the case of having characteristic parameters of the part of the plasma the radiation of which is detected by the system, step 1 is performed taking the values of said parameters.

5. Method according to claim 2, where step b) of estimating an initial electron density value $N_{e,0}^z$ is performed by means of the Stark broadening-based method.

6. Method according to claim 2, where step c) of estimating an initial temperature value $T_0^z$ (z=0, 1) is performed by means of the Boltzmann diagram method.

7. Method according to claim 3, where step b) of estimating an initial electron density value $N_{e,0}^z$ is performed by means of the Stark broadening-based method.

8. Method according to claim 3, where step c) of estimating an initial temperature value $T_0^z$ (z=0, 1) is performed by means of the Boltzmann diagram method.

\* \* \* \* \*